United States Patent [19]
Salazar et al.

[11] Patent Number: 5,213,500
[45] Date of Patent: May 25, 1993

[54] STRESS ABSORBING SEMIPERMANENT DENTAL IMPLANT SYSTEM

[76] Inventors: Alfred Salazar, 17406 S. 92 E. Ave., Bixby, Okla. 74008; Ricardo Guerra, 4455 N. Newcastle, Hardwood Heights, Ill. 60656

[21] Appl. No.: 927,805

[22] Filed: Aug. 10, 1992

[51] Int. Cl.$^5$ ............................................... A61C 8/00
[52] U.S. Cl. ...................................... 433/169; 433/173
[58] Field of Search .................................. 433/169, 173

[56] References Cited

U.S. PATENT DOCUMENTS

| | | | |
|---|---|---|---|
| 3,344,522 | 10/1967 | Wasserman | 433/169 |
| 3,955,280 | 5/1976 | Sneer | 433/169 |
| 4,622,010 | 11/1986 | Koch | 433/173 |
| 4,881,897 | 11/1987 | Franek et al. | 433/169 |
| 4,938,693 | 7/1990 | Bulakiev | 433/169 |
| 4,950,161 | 8/1990 | Richter | 433/173 |
| 4,957,437 | 9/1990 | Shimura et al. | 433/169 |
| 5,049,073 | 9/1991 | Lauks | 433/169 |

Primary Examiner—John J. Wilson
Attorney, Agent, or Firm—Veo Peoples, Jr.

[57] ABSTRACT

A dental implant system comprising a foundation fixture to be embedded in the jaw bone; said system further comprising a hollow transmucosal abutment member supporting a keeper for either a single tooth prosthesis or multiple teeth prostheses. The abutment comprises a plurality of inwardly curved resilient members defining a hollow column extending from a series of external threads which connect, in torus-like fashion, to a hollow pedestal section for the abutment. The internal surfaces of the resilient members have configured protrusions configured to interlock with the keeper. This configuration, in a no-load condition, allows the keeper to rest within the foundation fixture at sufficiently spaced-apart relationship between the keeper and the fixture to maintain a shock-absorbing fluid reservoir. An elastic seal is fitted between the keeper base and the pedestal of the abutment for closure of the reservoir.

7 Claims, 2 Drawing Sheets

STRESS ABSORBING SEMIPERMANENT DENTAL IMPLANT SYSTEM

BACKGROUND OF THE INVENTION

1. Field of the Invention

The present invention relates to a dental implant. More specifically, this invention relates to an endosteal root-form implant system with hydraulic and mechanical means to mimic the movement and shock-absorbing characteristics of natural teeth.

2. Brief Description of the Prior Art

Since the dawn of civilization, man has been concerned with the partial or total lack of teeth: first for aesthetic, then for practical reasons.

The study of Egyptian mummies from the Middle Kingdom up to the Ptolemys showed unusual processes of dental implantation. Some had substitutions derived from the cadaver,s teeth or sculptured ivory taken from the tusks of different animals. This practice was maintained through medieval times.

A scientific breakthrough in the area of dental implants was achieved by Professor Per-Ingvar Branemark and co-workers. By combining a two-stage surgical technique with the use of titanium fixtures, these scientists achieved predictable results in surgical placement of endosteal-route-form implants. In their continued studies in the early 1960s, these same scientists laid the foundation for modern implantology.

However, because of the lack of periodontal ligaments between the bone and the titanium fixture, such prior art implants do not have the natural motion and shock-absorbing capability of natural teeth.

Screw attachments have been used as shock absorbers but under stress tend to fracture. In a publication entitled "Dental Implant Prosthodontics" (J. B. Lippincott Company 1991 ISBN 0-397-51045-4), one of the authors, Ronald P. Desjardins, observes, "The most common prosthesis problem that the author has thus far noted is the loosening or breakage of the gold locking screw with the resultant loosening of the prosthesis."

In the early 1970s, Dr. Kirsch from Germany designed an implant system called IMZ with a plastic shock-absorber called IME. This device provided elastic properties similar to the periodontal ligament. The IME, an inside and outside threaded intermediary sleeve, is installed inside of the implant by screwing it into the threaded bore of the bone fixture. The sleeve itself has an internal threaded bore, into which a prosthesis is screwed.

However, in the same publication mentioned above, this time Robert J. Chapman observes, "The IME must be replaced every year or two, however, because it is plastic and will deteriorate somewhat with function." That deterioration of the plastic sleeve opens a way for bacteria and changes the mechanical characteristics of this device. U.S. Pat. No. 4,622,010 describes a similar device that avoids the threads on the plastic sleeve.

U.S. Pat. No. 4,993,950 describes a keeper system which uses an 0-ring "to permit universal 'rocking' motion of the keeper member relative to the true transmucosal cuff."

U S. Pat. No. 5,006,068 describes a dental implant system with a resilient force-dampening means on the prosthesis itself.

These prior art designs provide only a single means of shock-absorbing capacity. They fail to imitate the longitudinal movement of natural teeth. Prior art implant systems also fail in other respects. Such systems feel unnatural to the person using such prior art dental implant systems when the prosthesis is cemented between a natural tooth abutment and an implant abutment. Furthermore, the cement will be placed under great torquing stress at both ends of the prosthesis. This torquing stress tends to break the cement and cause the failure of the prosthesis.

An important safety feature of the natural tooth has been overlooked by the prior art. If by accident a natural tooth receives a frontal impact which is strong enough to put in jeopardy the integrity of the jaw bone, nature has chosen to loose one or more teeth to preserve the integrity of the jaw bone from major damage.

An object of the present invention is to provide a dental implant system which is able t relieve the prosthesis when impacted by excessive force.

A further object of the present invention is to provide an implant system which mimics the shock-absorbing capabilities of natural teeth, including mimicking the loosening of tooth from the jaw bone.

A further object of the present invention is to provide an implant system which mimics the longitudinal movement of natural teeth.

A still further object of the present invention is to provide a reliable implant system which is safe and relatively inexpensive to manufacture.

SUMMARY OF THE INVENTION

A two-stage surgical procedure, which is typical of endosteal root-form implanting is well known in the prior art and will be summarily mentioned in this description.

We summarize that, in stage one, the surgeon cuts a flap on the mucosa and drills a socket on the bone, where the foundation fixture is implanted with a healing screw. The soft tissue is repositioned and the implant site is closed to avoid any movement of the fixture and to prevent infection. In stage two, after osseointegration is complete, the surgeon uncovers the healing screw and replaces it with a transmucosal abutment where different prosthesis can be attached by different means.

The present invention relates to a dental implant system comprising a foundation fixture to be embedded in the bone, having attached a hollow transmucosal abutment member which, in turn, holds a keeper for a single tooth prosthesis or for multiple teeth prostheses.

This implant system is characterized by three dampening means to attenuate the tensile, compressive and shearing forces received by the prosthesis during chewing or during other impact. Such dampening action more effectively mirrors the action of natural teeth in both tooth movement and tooth shock-absorbing characteristics, without the need for an extraneous element to emulate a periodontal ligament.

The first dampening means is derived from a novel juxtaposition between the keeper and a socket configured within the foundation fixture.

The second dampening means is derived from a novel interlocking resiliency at the abutment/keeper interface.

The third dampening means is derived from the elasticity of a seal interposed between the base of the keeper and the pedestal of the abutment where they come together at the prosthesis.

BRIEF DESCRIPTION OF THE DRAWINGS

The invention will be more fully understood with reference to the accompanying drawings and the explanations thereof.

DETAILED DESCRIPTION AND PREFERRED EMBODIMENTS

Figure 1:
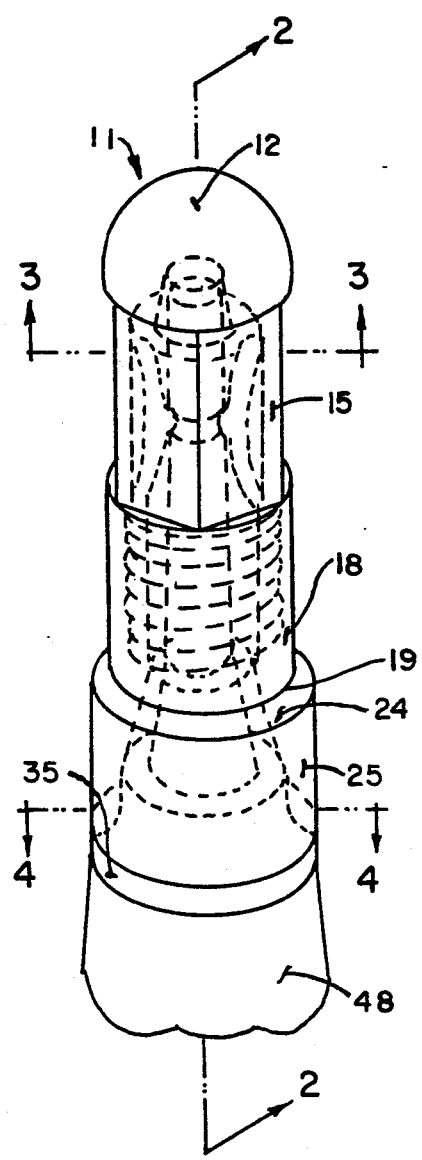
FIG. 1 is a perspective view of the preferred embodiment for a single tooth prosthesis implant system of the present invention for installation in the upper jaw.
Figure 5:
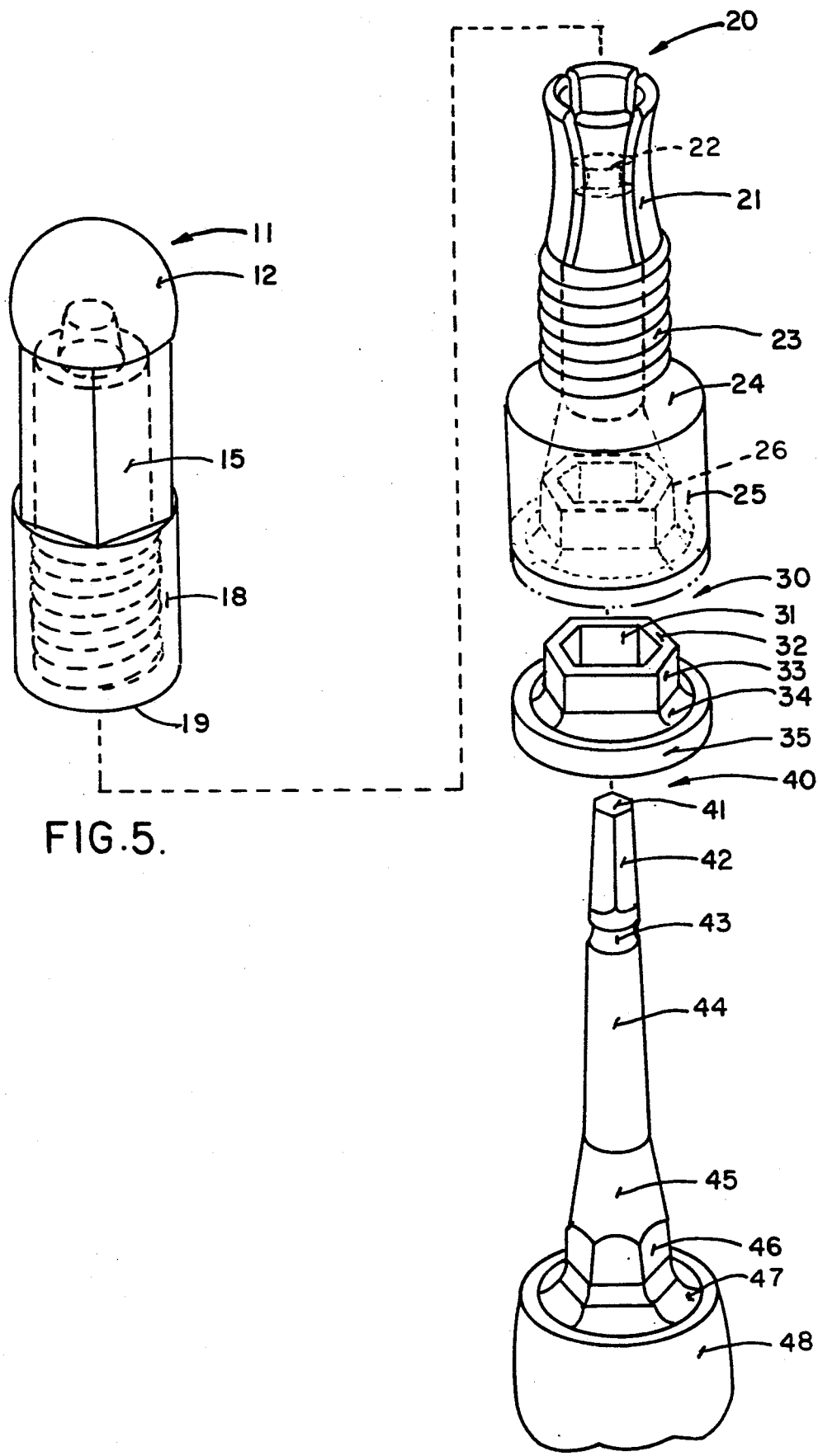
FIG. 5 is a disassembled perspective view of that preferred embodiment.

FIG. 1 illustrates a fully assembled single tooth prosthesis dental implant for installation in the upper jaw. Referring to FIG. 5, the four primary parts of the implant system of the present invention and their sequence of assembly can be seen; i.e., the foundation fixture 11, the intramucosal abutment 20, the seal 30 and the keeper 40. These parts are made of materials with chemical, physical, and biological characteristics adapted for implantation into the oral cavity. Commercially pure titanium, and certain medical grade titanium alloys are preferred for the fixture 11, the abutment 20 and the keeper 40 of the present invention. The fixture 11 is preferably coated with hydroxyapatite.

The fixture 11 as shown in FIG. 5 preferably has a heavily textured outside surface which increases the surface area and allows bone ingrowth. It is comprised of closed domed end 12, a middle body 15 extending vertically from 12, a base 18, and an open end 19. The closed end 12 of the fixture 11 is preferably hemispherical or domed-shape, because this shape diffuses the masticatory forces. The domed end leads the implantation into the jaw bone. The middle body section 15 is multi-sided, preferably hexagonal, so as to resist torque and to improve the anchorage capability of the fixture, after osseointegration is achieved. The base 18 extends from middle body 15 opposite of the dome 12, and said base 18 at its bottom end 19 is open for receiving the abutment 20.

The hollow internal configuration of the foundation fixture 11 may be more readily described by reference to FIG. 2. A horizontal internal wall 13 and vertical internal walls 14, preferably tapered inward toward dome 12, and extending downward from 13 define an allen wrench-type socket within the closed dome end 12. A vertical internal cylindrical wall 16 extends downward from the socket and has a diameter slightly wider than the width of the socket. Extending downward from the cylindrical wall 16 are a series of internal threads 17 (see also FIG. 5) which serve to define the internal surface of the base 18 of the foundation fixture. A bottom opening 19, seen at FIG. 5, is defined by inwardly tapered internal surface extending from internal threads 17.

The abutment 20, as may be seen at FIG. 5 of the present invention, comprises a hollow column at one end defined by four or more elastic resilient members 21 with an inward curvature, which members function as leaf springs. Each of these members 21 have affixed a protruding element 22 (as more clearly shown on FIG. 2) at their inner surface. The hollow column is further defined by external threads 23 which extend in torus-like fashion between the members 21 and tapered shoulder 24 which connects a hollow pedestal 25 whose inner surface is defined by a recessed opening 26 (also referred to as an abutment socket) with walls tapered outward to fittingly engage a seal 30. The seal 30 (shown at FIG. 5) is secured tightly within an abutment socket 26.

The pedestal base 25 is the intramucosal area of the abutmen 20 and is therefore highly polished to better control plaque.

The seal 30 of the present invention is preferably composed of high-quality silicon rubber and should be resistant to the different temperatures, acids and oils common to the oral cavity and to the shock-absorbing fluid present inside of the implant. Vertical flat walls 33 of the seal body form a hexagonal shape and connect horizontal surface 32 which define the hexagonal opening 31. Within opening 31 the seal is preferably constructed of sponge-like material or material containing small air bubbles for cushioning purposes. The outside skin at 33 is impermeable to air. Extending laterally from walls 33 is a circumferential bottom web 34 extending to bottom circular shoulder 35. The side face of this shoulder 35 is the outside seal surface that keeps the saliva out of the implant.

At FIG. 5, it can be seen that the keeper 40 has a long shaft including sections 41, 43, 44, 45 and 46 with an overall length equivalent to the root of a natural tooth. This characteristic is very important to imitate the natural longitudinal movement of a tooth and to avoid a "rocking" motion as in some systems in the prior art such as U.S. Pat. No. 4,756,689, U.S. Pat. No. 4,993,950 and U.S. Pat. No. 5,006,068.

It will be readily understood by those skilled in the art that the movement achieved by the keeper 40 of the present invention precisely imitates the movement of natural teeth. The importance of this capability is not only for the natural feeling of the patient but is of great functional importance whether the implant is going to hold one end of a prosthesis bridge or a single prosthesis tooth 48. The natural tooth-like action of the prosthesis 48 is desired to avoid stress on the adjacent natural teeth. From the bottom hexagonal neck 47 of the keeper to its top end 41, the keeper of the present invention has a gradual conical tapering of 46, 45, 44 and 42. This design provides improved safety. It facilitates the expulsion of the keeper from the implant system in the event of an accident such as extreme frontal force hitting the prosthesis and endangering the integrity of the jaw bone. This also permits the implant system of the present invention to more closely mimic the action of natural teeth than previously achieved in the prior art.

Figure 2:
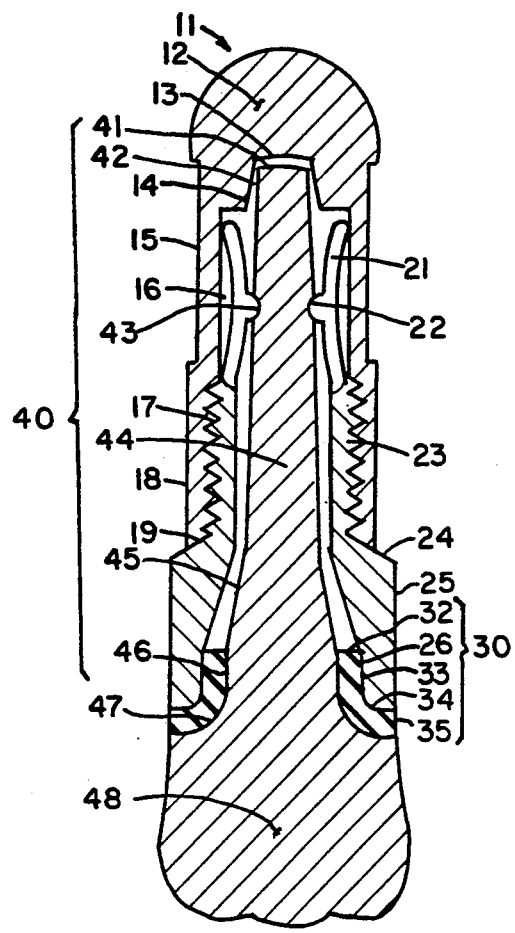
FIG. 2 is a sectional view of the same preferred embodiment taken along line 2—2 of FIG. 1.
Figure 3:
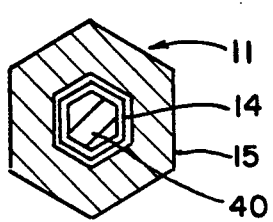
FIG. 3 is a sectional view of that preferred embodiment taken along line 3—3 of FIG. 1.
Figure 4:
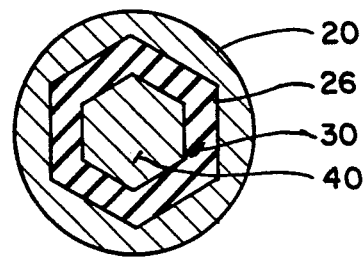
FIG. 4 is a sectional view of that preferred embodiment taken along line 4—4 of FIG. 1.

FIG. 2 shows the internal cross section 48 of a prosthesis tooth, forming one single unit with the keeper 40. However, other kinds of dental prosthesis such as a bridge may be secured to the keeper 40 by this general means, where multiple natural teeth-like action is desired.

ASSEMBLY AND OPERATION

In the first stages of dental implantation the foundation fixture 11 is implanted into the jaw bone with domed section 12 leading the insertion. A healing screw (not shown) is installed through opening 19 and secured by internal threads 17. In the second stage, after osseointegration, the healing screw is removed and the shock-absorbing liquid is introduced in the fixture in desired amount with a graduated hypodermic syringe and protected from escaping during remainder of assembly. The fluid can be, for example, inorganic or organic, non-toxic, stable compounds, such as petrolatum, etc., which are capable of functioning as hydraulic, shock-absorbing lubricants.

The remainder of the implant is assembled and inserted into the fixture while retaining a reservoir of the shock-absorbing lubricant within the implant. More particularly, with reference to FIG. 5, the prosthesis shoulder 47 and keeper 40 assemblage is inserted through the seal 30, whose hexagonal orifice 31 engagably receives the hexagonal neck 46 of the keeper 40. The end 41 of the keeper and seal assemblage is then telescoped through the abutment socket opening 26 of the abutment 20 until the socket 26 fittingly engages the side walls 33 of the seal 30, and the protrusions 22 of the abutment engage the groove 43 of the keeper. This assemblage can be inserted into the fixture opening 19 and internal threads 17 of the fixture screw-wise engaged with the external threads 23. Referring once again to FIG. 2, the fully assembled implant will then offer a first dampening means deriving from the juxtaposition between the end 41 of the keeper 40 and the socket formed by walls 13 and 14 of the fixture 11. That is, at the no-load condition (absence of masticatory forces), end 41 is pivotally positioned in spaced-apart relationship from the walls of the socket, and the space therebetween is filled with shock-absorbing lubricant. This allows end 41 to pivot longitudinally within the fluid-filled space in a manner that mimics natural tooth movement. This configuration also during the chewing stroke assists to inhibit rotation or twisting of the end 42, and when the keeper end 41 vertically plunges slightly into the socket formed by walls 13 and 14, closing the space between 41 and the socket, the fluid considerably absorbs the downward stress.

Referring also to FIG. 2, a second force dampening means is provided from the novel interlocking resiliency at the abutment protrusion 22/keeper groove 43 interface. The circumferential groove 43 between sections 42 and 44 of the keeper 40, interlockingly resilient members 21 of the abutment 20 by a "snap action" of the protrusions 22 at the resilient member's inner surface. The resilient members themselves dampen longitudinal forces. Furthermore, during the downward chewing stroke, the upward movement of the keeper 40 pushes the protrusions 22 partially up and out of the groove 43, forcing the resilient members 21 outward and displacing the shock-absorbing fluid. These members 21 store some of the energy from the downward chewing stroke and releases that energy back during the upward stroke when there is no-load and the protrusions 22 return to groove 43. Furthermore, this configuration assists in holding the keeper end 41 apart from the socket 14 at the no-load condition, thus permitting the shock absorber fluid to return to the socket space. Also, the interlock asserts a contributing force against the seal 30 to help it resist leakage.

Some prior work, U.S. Pat. No. 3,722,094 and U.S. Pat. No. 4,881,897 have made use of a coil spring as resilient member. However, those skilled in the art can appreciate how cumbersome, and risky, the installation of such coil springs in the oral cavity can be.

Coil springs release the pressure o the bottom of the fixture, while the leaf springs of the present invention form a single unit with the abutment which is supported by the lateral walls of the implant and dissipate some of the vertical forces in a horizontal direction. This action is very important because reduction in occlusal force renders the implant of this invention ideal for use as a splint for the remaining teeth.

Referring also to FIG. 2 and to FIG. 5, the seal 30 keeps the shock-absorbing fluid inside of the implant and saliva out of it. The seal also absorbs shearing and compression forces and thus serves as the third shock-absorbing or dampening means. The seal at opening 31 fits into the hexagonal neck 46 of the keeper 40. A top face 32 of the seal 30 seals the fluid inside the implant. The seal dampens compression, torque and shearing forces, allowing more natural longitudinal movement of keeper 40. The seal is compressed during the chewing stroke and its elasticity allows it to release during the upward stroke, which release action assists in pumping the shock-absorbing fluid back to its no-load position.

The shock-absorbing fluid (not shown) is preferably a dense compound at body temperature. This fluid is preferably an inorganic, non-toxic, lubricant, antibacterial fungicide to inhibit bacterial growth. The fluid can therefore serve three functions: first, it can be a moisturizer for the inside face 32 of the seal 30 to keep it from drying out. Dryness of the seal causes cracks and deterioration of the seal qualities. Second, it can serve as a lubricant to reduce friction, friction noises and premature wear of any metal parts of the implant. Third, as a shock-absorbing fluid, it will absorb the intensity of, and inhibit damage from, a "hard bite". Fluid friction is nearly proportional to the square velocity of the applied force.

What is claimed is:

1. A dental implant system comprising:
   a. a foundation fixture having an internal socket in spaced-apart relationship from one end of an elongated keeper, said spaced-apart relationship defining a shock-absorbing fluid reservoir force dampening means; and
   b. a transmucosal abutment telescopically fitted within said foundation fixture, said abutment comprising a plurality of vertical resilient members having protrusions at their inner surface and defining a hollow column extending from external threads which further define the hollow column and said threads configured in torus-like fashion above a hollow pedestal member of the abutment; and
   c. a keeper extending telescopically through the abutment and at one end resting within the fixture socket, said keeper having a circumferential circular groove to releaseably receive by "snap-action" the protrusions of the abutment so as to define a second dampening means, and having a web-like base fitted to a single or multiple tooth prostheses; and
   d. a seal member fitted between the web-like base of the keeper and the pedestal of the abutment so as to form a third force dampening means;

whereas the implant more effectively mirrors the longitudinal movement of natural teeth, mimics the shock-absorbing capabilities of natural teeth, and relieves the prosthesis when impacted by excessive force without injuring the jawbone.

2. The system of claim 1 wherein the shock-absorbing fluid is an antibacterial fungicide.

3. The system of claim 1 wherein the keeper has a gradual conical tapering shape to facilitate expulsion from the implant in the event of an extreme frontal force.

4. The system of claim 1 wherein the foundation fixture comprises a closed dome-shaped end, a hexagonal middle body, and a cylindrical end opposite the domed end.

5. The system of claim 1 wherein the resilient members of the abutment are at least four in number.

6. The system of claim 1 wherein the resilient members are inwardly bent leaf springs.

7. The system of claim 1 wherein the shock-absorbing fluid is petrolatum.

* * * * *